US00PP21328P2

(12) United States Plant Patent
Schenk

(10) Patent No.: US PP21,328 P2
(45) Date of Patent: Sep. 28, 2010

(54) LILY PLANT NAMED 'SUNNY OKINAWA'
(50) Latin Name: ***Lilium* L.**
Varietal Denomination: Sunny Okinawa

(75) Inventor: Pieter Cornelis Schenk, Wieringerwerf (NL)

(73) Assignee: MAK Breeding Rights B.V., Wieringerwerf (NL)

( * ) Notice: Subject to any disclaimer, the term of this patent is extended or adjusted under 35 U.S.C. 154(b) by 0 days.

(21) Appl. No.: 12/454,417

(22) Filed: May 18, 2009

(51) Int. Cl.
*A01H 5/00* (2006.01)

(52) U.S. Cl. ..... Plt./315
(58) Field of Classification Search ..... Plt./315
See application file for complete search history.

*Primary Examiner*—June Hwu
(74) *Attorney, Agent, or Firm*—C. A. Whealy

(57) ABSTRACT

A new and distinct cultivar of Lily plant named 'Sunny Okinawa', characterized by its upright and compact plant habit; vigorous growth habit; densely-foliated habit; freely flowering habit; upright flower buds; white-colored flowers; and good postproduction longevity.

1 Drawing Sheet

Botanical designation: *Lilium* L.
Cultivar denomination: 'Sunny Okinawa'.

BACKGROUND OF THE INVENTION

The present Invention relates to a new and distinct cultivar of Lily plant, commercially known as Oriental Hybrid Lily, botanically known as *Lilium* L., and hereinafter referred to by the name 'Sunny Okinawa'.

The new Oriental Hybrid Lily plant is a product of a planned breeding program conducted by the Inventor in Wieringerwerf, The Netherlands. The objective of the breeding program was to develop new compact and dense potted Oriental Hybrid Lily plants with large flowers, attractive flower coloration and good postproduction longevity.

The new Oriental Hybrid Lily plant originated from a cross- pollination in 2001 of a proprietary selection of *Lilium* L. identified as code number XB-275P, not patented, as the female, or seed, parent with a proprietary selection of *Lilium* L. identified as code number XA-413P, not patented, as the male, or pollen, parent. The new Oriental Hybrid Lily plant was discovered and selected by the Inventor as a flowering plant from within the resultant progeny of the cross-pollination in a controlled greenhouse environment in Wieringerwerf, The Netherlands in July, 2005.

Asexual reproduction of the new Oriental Hybrid Lily plant by bulb scales in a controlled greenhouse environment in Wieringerwerf, The Netherlands since November, 2005, has shown that the unique features of this new Oriental Hybrid Lily plant are stable and reproduced true to type in successive generations.

SUMMARY OF THE INVENTION

Plants of the new Oriental Hybrid Lily have not been observed under all possible environmental conditions. The phenotype may vary somewhat with variations in environment such as temperature and light intensity without, however, any variance in genotype.

The following traits have been repeatedly observed and are determined to be the unique characteristics of 'Sunny Okinawa'. These characteristics in combination distinguish 'Sunny Okinawa' as a new and distinct cultivar of Oriental Hybrid Lily plant:

1. Upright and compact plant habit.
2. Vigorous growth habit.

3. Densely-foliated habit.
4. Freely flowering habit.
5. Upright flower buds.
6. White-colored flowers.
7. Good postproduction longevity.

Plants of the new Oriental Hybrid Lily differ primarily from plants of the female parent selection primarily in the following characteristics:

1. Plants of the new Oriental Hybrid Lily are more compact than plants of the female parent selection.
2. Plants of the new Oriental Hybrid Lily have narrower leaves than plants of the female parent selection.

Plants of the new Oriental Hybrid Lily differ primarily from plants of the male parent selection primarily in the following characteristics:

1. Plants of the new Oriental Hybrid Lily are larger than plants of the male parent selection.
2. Plants of the new Oriental Hybrid Lily are more freely flowering than plants of the male parent selection.

Plants of the new Oriental Hybrid Lily can be compared to plants of Oriental Hybrid Lily 'Souvenir', not patented. Plants of the new Oriental Hybrid Lily differ from plants of 'Souvenir' in the following characteristics:

1. Plants of the new Oriental Hybrid Lily are more densely foliated than plants of 'Souvenir'.
2. Plants of the new Oriental Hybrid Lily have larger flowers than plants of 'Souvenir'.
3. Plants of the new Oriental Hybrid Lily have white-colored flowers whereas plants of 'Souvenir' have light pink-colored flowers.

Plants of the new Oriental Hybrid Lily can also be compared to plants of Oriental Hybrid Lily 'Mona Lisa', disclosed in U.S. Plant Pat. No. 7,379. Plants of the new Oriental Hybrid Lily differ from plants of 'Mona Lisa' in the following characteristics:

1. Plants of the new Oriental Hybrid Lily are more densely foliated than plants of 'Mona Lisa'.
2. Plants of the new Oriental Hybrid Lily and 'Mona Lisa' differ in flower color as plants of 'Mona Lisa' have light pink-colored flowers.

DESCRIPTION OF THE PHOTOGRAPH

The accompanying colored photograph illustrates the overall appearance of the new Oriental Hybrid Lily plant, showing the colors as true as it is reasonably possible to obtain in colored reproductions of this type. Colors in the photograph may differ slightly from the color values cited in the detailed botanical description which accurately describe the colors of the new Oriental Hybrid Lily plant. The photograph comprises a side perspective view of a typical flowering plant of 'Sunny Okinawa' grown in a container.

DETAILED BOTANICAL DESCRIPTION

The aforementioned photograph and following observations and measurements describe plants that were grown during the spring in a glass-covered greenhouse in Wieringerwerf, The Netherlands and under cultural conditions typically used in Oriental Hybrid Lily production. During the production of the plants, day temperatures were about 15° C., night temperatures were about 18° C. and light levels were about 6,000 lux. Measurements and numerical values represent averages for typical flowering plants. Plants were six months old when the photograph and description were taken. In the following description, color references are made to The Royal Horticultural Society Colour Chart, 2001 Edition, except where general terms of ordinary dictionary significance are used.

Botanical classification: *Lilium* L. Sunny Okinawa'.

Parentage:

*Female, or seed, parent.*—Proprietary selection of *Lilium* L. identified as code number XB-275P, not patented.

*Male, or pollen, parent.*—Proprietary selection of *Lilium* L. identified as code number XA-413P, not patented.

Plant description:

*Plant form/growth habit.*—Upright flowering plant; single erect flowering stem with a terminal cluster of flowers; compact and dense plant habit; vigorous growth habit.

*Plant height, soil level to top of flowers.*—About 21.5 cm.

*Plant diameter.*—About 19 cm.

*Plant circumference.*—About 60 cm.

*Bulbs.*—Diameter: About 10 cm to 20 cm. Texture: Smooth. Color: Close to 155D.

*Flowering stems.*—Diameter: About 1 cm. Internode length: About 1 cm. Strength: Strong. Texture: Smooth, glabrous. Color: Close to 138C.

*Leaves.*—Arrangement: Alternate; simple; sessile. Quantity of leaves per plant: About 43. Length, lower leaves: About 7 cm. Width, lower leaves: About 3 cm. Length, upper leaves: About 11.5 cm. Width, upper leaves: About 3.5 cm. Shape: Lanceolate. Apex: Acute. Base: Decurrent. Margin: Entire. Texture, upper and lower surfaces: Glabrous, smooth; leathery. Venation pattern: Parallel. Color: Developing and fully expanded leaves, upper surface: Close to 139A; venation, close to 139A. Developing and fully expanded leaves, lower surface: Close to 137B; venation, close to 137B.

Flower description:

*Flower arrangement.*—Flowers umbellate.

*Flower shape and aspect.*—Flowers are funnel-shaped and when fully opened, flatten and recurve towards the apex; flower buds face upright and flowers face mostly upright.

*Flowering habit.*—Freely flowering habit, large bulbs will produce seven to eight flowers per flowering stem.

*Fragrance.*—Slightly fragrant.

*Natural flowering season.*—Plants flower in June and July in The Netherlands. Plants can be flowered year-round in the greenhouse and forced to bloom about 110 days after planting bulbs.

*Postproduction longevity.*—Good postproduction longevity, flowers last about 10 to 15 days on the plant; tepals not persistent; gynoecium persistent.

*Flower buds.*—Length: About 8 cm. Diameter: About 3 cm. Circumference: About 10 cm. Shape: Lanceolate. Color: Close to 145B, with development close to 150D to 155D; sutures, close to 145A.

*Flower size.*—Diameter: About 16 cm. Length (height): About 3 cm. Throat length: About 2.5 cm.

*Perianth.*—Quantity/arrangement: Six tepals per flower; tepals imbricate. Tepal length, inner tepals: About 9 cm. Tepal width, inner tepals: About 5 cm. Tepal length, outer tepals: About 10 cm. Tepal width, outer tepals: About 3.8 cm. Tepal shape: Lanceolate. Tepal apex: Acute. Tepal margin: Entire. Tepal texture, upper and lower surfaces: Smooth, glabrous. Tepal color: When opening, upper and lower surfaces: Close to 155D. Fully opened, upper and lower surfaces: Close to 155D.

*Pedicels.*—Angle: About 45° from vertical. Strength: Strong. Length: About 2 cm. Diameter: About 5 mm. Texture: Smooth, glabrous. Color: Close to 137C.

*Reproductive organs.*—Stamens: Quantity per flower: About six. Filament length: About 7.5 cm. Filament color: Towards the base, close to 145D; towards the apex, close to 149D. Anther length: About 2 cm. Anther color: Close to 180A. Pollen color: Close to 32A. Pistils: Quantity per flower: One. Pistil color: Close to 79D. Style length: About 7 cm. Style color: Close to 145A to 145C.

*Fruits.*—Length: About 2 cm. Diameter: About 5 mm. Color: Close to 145B.

*Seed produced.*—No viable seeds observed.

Disease/pest resistance: Resistance to pathogens and pests common to Oriental Lilies has not been observed.

Garden performance: Plants of the new Oriental Hybrid Lily have exhibited good tolerance to rain and wind and have been observed to tolerate temperatures from about −2° C. to about 40° C.

It is claimed:

1. A new and distinct Lily plant named 'Sunny Okinawa' as illustrated and described.

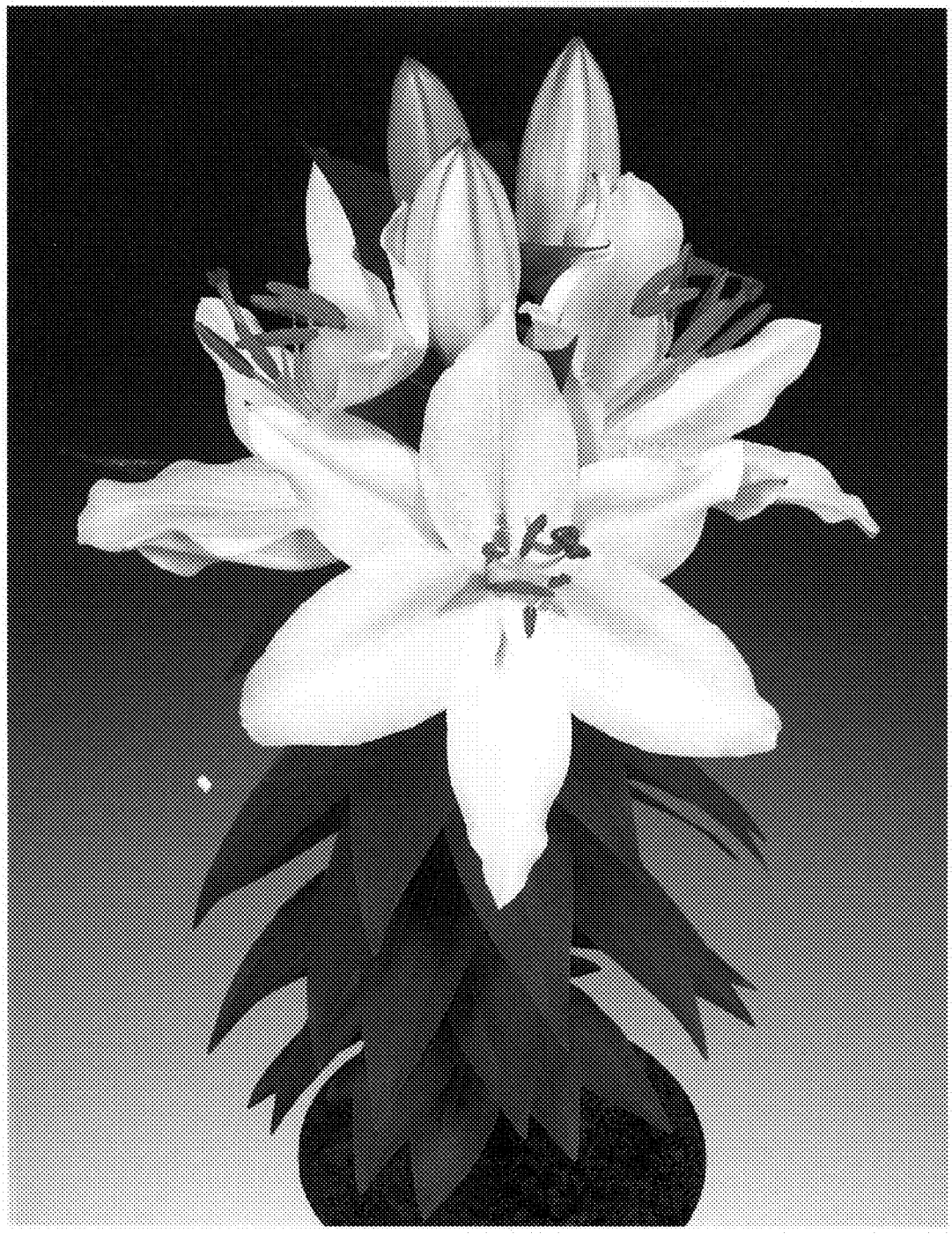

* * * * *